(12) United States Patent
Yamamoto et al.

(10) Patent No.: US 7,518,125 B2
(45) Date of Patent: Apr. 14, 2009

(54) PROCESSING APPARATUS USING FOCUSED CHARGED PARTICLE BEAM

(75) Inventors: Yo Yamamoto, Chiba (JP); Haruo Takahashi, Chiba (JP); Toshiaki Fujii, Chiba (JP)

(73) Assignee: SII NanoTechnology Inc. (JP)

( * ) Notice: Subject to any disclaimer, the term of this patent is extended or adjusted under 35 U.S.C. 154(b) by 206 days.

(21) Appl. No.: 11/501,629

(22) Filed: Aug. 9, 2006

(65) Prior Publication Data

US 2007/0040128 A1   Feb. 22, 2007

(30) Foreign Application Priority Data

Aug. 19, 2005   (JP)   ............... 2005-238632

(51) Int. Cl.
  *G01N 23/00*   (2006.01)

(52) U.S. Cl. ................................. 250/443.1
(58) Field of Classification Search .............. 250/443.1, 250/492.21, 309, 310
See application file for complete search history.

(56) References Cited

U.S. PATENT DOCUMENTS 7,053,370 B2 *   5/2006   Motoi et al. ................. 250/306
7,304,302 B1 *   12/2007   Nunan et al. ................ 250/311

* cited by examiner

*Primary Examiner*—Kiet T Nguyen
(74) *Attorney, Agent, or Firm*—Adams & Wilks

(57) ABSTRACT

A processing apparatus uses a focused charged particle beam to process a micro sample that is supported on a micro mount part. The micro mount part is supported on a micro sample stage and locally cooled by a cooling unit. The micro mount part is thermally independent of the micro sample stage and, due to its small size, can be cooled rapidly by the cooling unit.

18 Claims, 4 Drawing Sheets

PROCESSING APPARATUS USING FOCUSED CHARGED PARTICLE BEAM

BACKGROUND OF THE INVENTION

The present invention relates to a processing apparatus which has a cooling sample stage allowing reduction of thermal drift and which uses a focused charged particle beam.

In recent years, in preparing a sample for an electronic microscope in order to observe a particular area such as observing a defective part of a semiconductor device, a method of using a charged particle beam is utilized. More specifically, a sample is processed in such ways that ions are accelerated, focused and applied onto a particular area of a device or the like to be an observation target and a desired slice is cut out, and that a sample is cut to provide desired depth or a shape in order to expose an observation part when an observation target exists inside.

When a sample to be an observation target is a material vulnerable to heat, it is necessary to process the sample while it is being cooled. In addition, charged particle beam irradiation often damages a sample, but it is reported that a sample is cooled to reduce damage caused by a charged particle beam.

At present, when a sample is cooled in a charged particle beam processing apparatus, a sample state is cooled for processing. Here, typically, when a sample is cooled, the entire sample stage is cooled. However, when the entire sample stage is cooled, problems arise that it takes a long time to stabilize the temperature of a sample, and that cooling the entire sample tends to generate a temperature gradient and thus a drift tends to occur caused by thermal expansion and contraction, causing highly accurate processing to be difficult. For the measures against the drift, there is a method in which the temperature of a sample is set to a desired temperature beforehand and the structure of the surface and the cross section and the information of the sample are acquired for accurate observation or processing. However, the equipment becomes in a large scale, and the method is not a convenient method for solving problems.

[Patent Reference 1] JP-A-2003-194746

The invention has been made in view of the circumstances. An object is to provide a processing apparatus which uses a focused charged particle beam and which can promptly cool a sample, reduce a thermal drift, suppress a position shift caused by thermal expansion and contraction, and improve processing accuracy.

SUMMARY OF THE INVENTION

A first aspect according to the invention is a processing apparatus using a focused charged particle beam characterized by including: a micro sample stage having a micro mount part on which a micro sample is placed, the micro sample is processed with the focused charged particle beam, wherein the micro mount part is thermally independent of the micro sample stage and has a cooling unit which cools the micro mount part.

In the first aspect, since the sample and the mount stage are minute, they can be cooled promptly. Since the contraction displacement caused by cooling is small, a thermal drift can be reduced to improve processing accuracy.

A second aspect according to the invention is the processing apparatus using the focused charged particle beam in the first aspect, characterized by including a sample stage on which a sample is placed, the sample is processed with the focused charged particle beam.

In the second aspect, since the micro sample stage and the sample stage are provided, the micro sample and the sample can be handled at the same time.

A third aspect according to the invention is the processing apparatus using the focused charged particle beam in the first or second aspect, characterized in that the micro sample is cut out of the sample.

In the third aspect, the micro sample can be cut out of any places in the sample in any size and any shapes, and it can be processed or observed while it is being cooled on the micro mount part.

A fourth aspect according to the invention is the processing apparatus using the focused charged particle beam in any one of the first to third aspects, characterized by including a micro sample stage which is formed of a material having a lower heat conduction than that of the micro mount part.

In the fourth aspect, the micro sample stage formed of the material having a lower heat conduction than that of the micro mount part is provided, and thus heat conduction from the micro sample and the micro mount part to the micro sample stage can be prevented to effectively cool only the micro sample and the micro mount part.

A fifth aspect according to the invention is the processing apparatus using the focused charged particle beam in the fourth aspect, characterized in that the cooling unit is an electronic cooling mechanism which cools by supplying electric power thereto.

In the fifth aspect, the micro mount part is cooled by small-sized electronic cooling mechanism, and thus the micro sample can be cooled promptly.

A sixth aspect according to the invention is the processing apparatus using the focused charged particle beam in the fourth aspect, characterized in that the cooling unit is a probe in which a cooling medium is filled and which is abutted against the micro mount part.

In the sixth aspect, the micro mount part is cooled by a fine tube or the probe which contains a cooling medium and has the sharp tip end, and thus the micro sample can be cooled promptly.

A seventh aspect according to the invention is the processing apparatus using the focused charged particle beam in the fourth aspect, characterized in that the cooling unit is a cooling tube which is disposed on the micro mount part and through which a cooling medium flows.

In the seventh aspect, the micro mount part is cooled by the cooling tube which contains the cooling medium, and thus the micro sample can be cooled promptly.

An eighth aspect according to the invention is a processing apparatus using a focused charged particle beam characterized by including: a top plate on which a sample is placed, the sample being processed with the focused charged particle beam; and a bottom plate which is disposed in parallel with the top plate, wherein a special mount stage is formed by connecting the top plate to the bottom plate with a connecting member, the special mount stage is supported by a special mount stage support which is formed of a material having a lower heat conduction than the special mount stage, one of the top plate and the bottom plate is fixed on a special mount stage support side, and the connecting member is cooled, whereby a cooling unit is provided which directs thermal contraction directions of the top plate and the bottom plate in directions opposite to each other.

In the eighth aspect, since the connecting member of the top plate to the bottom plate is cooled, thermal contraction is directed in the opposite directions in the top plate and the bottom plate, and the drift amount is reduced. In addition, since the sample is not required to be the cut out micro sample, the drift amount is reduced even though a sample is greater than the micro sample.

A ninth aspect according to the invention is the processing apparatus using the focused charged particle beam in the eighth aspect, characterized by including a sample stage on which the sample is placed, the sample is processed with the focused charged particle beam.

In the ninth aspect, since the special mount stage and the sample stage are provided, a plurality of the samples can be handled at the same time.

A tenth aspect according to the invention is the processing apparatus using the focused charged particle beam in the eighth or ninth aspect, characterized in that the cooling unit is an electronic cooling mechanism which cools by supplying electric power thereto.

In the tenth aspect, the connecting member is cooled by electronic cooling mechanism, and thus the sample can promptly cooled.

An eleventh aspect according to the invention is the processing apparatus using the focused charged particle beam in the eighth or ninth aspect, characterized in that the cooling unit is a probe in which a cooling medium is filled and which is abutted against the micro mount part.

In the eleventh aspect, the connecting member is cooled by a fine tube or the probe which contains a cooling medium and has the sharp tip end, and thus the micro sample can be cooled promptly.

A twelfth aspect according to the invention is the processing apparatus using the focused charged particle beam in the eighth or ninth aspect, characterized in that the cooling unit is a cooling tube which is disposed on the micro mount part and through which a cooling medium flows.

In the twelfth aspect, the micro mount part is cooled by the cooling tube which contains the cooling medium, and thus the micro sample can be cooled promptly.

A thirteenth aspect according to the invention is the processing apparatus using the focused charged particle beam in any one of the first to seventh aspects, characterized by including a sample stage holder on which the sample stage or the micro sample stage is detachably placed.

In the thirteenth aspect, the sample stage or the micro sample stage can be replaced.

A fourteenth aspect according to the invention is the processing apparatus using the focused charged particle beam in the fifth or seventh aspects, characterized by including a sample stage holder on which the micro sample stage having the sample stage or the cooling unit is detachably placed, wherein the sample stage holder is provided with a contact which is connected to the cooling unit to supply a cooling source.

In the fourteenth aspect, the micro sample stage or the sample stage can be replaced, and the cooling mechanism can be detached.

A fifteenth aspect according to the invention is the processing apparatus using the focused charged particle beam in any one of the eighth to twelfth aspects, characterized by including a sample stage holder on which the sample stage or the special mount part support is detachably placed.

In the fifteenth aspect, the special mount part support or the sample stage can be replaced.

A sixteenth aspect according to the invention is the processing apparatus using the focused charged particle beam in the tenth or twelfth aspect, characterized by including a sample stage holder on which the micro sample stage having the sample stage or the cooling unit is detachably placed, wherein the sample stage holder is provided with a contact which is connected to the cooling unit to supply a cooling source.

In the sixteenth aspect, the micro sample stage or the sample stage can be replaced, and the cooling mechanism can be detached.

ADVANTAGE OF THE INVENTION

The processing apparatus using the focused charged particle beam according to the invention can promptly cool the sample and can relax a thermal drift by the special mount stage which can reduce the sample and the sample mount part in size and can reduce the position change of the mount stage caused by thermal expansion and contraction.

DETAILED DESCRIPTION OF THE INVENTION

Embodiments of the invention will be described in detail with reference to the drawings.

First Embodiment

Figure 1:
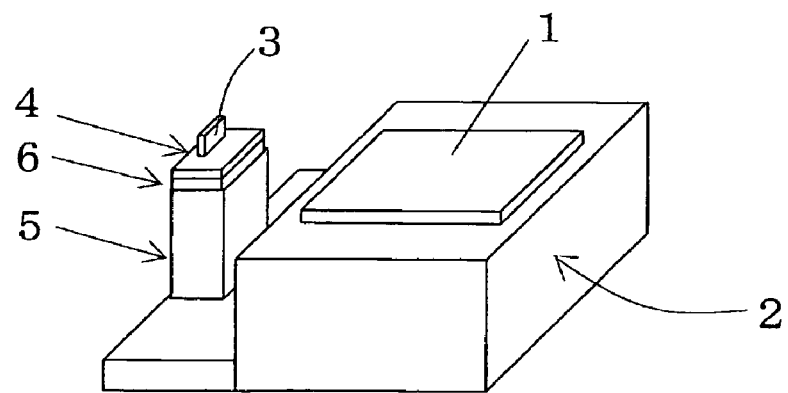
FIG. 1 is a perspective view depicting the micro sample stage and the sample stage of the processing apparatus using the focused charged particle beam according to the first embodiment of the invention.
Figure 2:
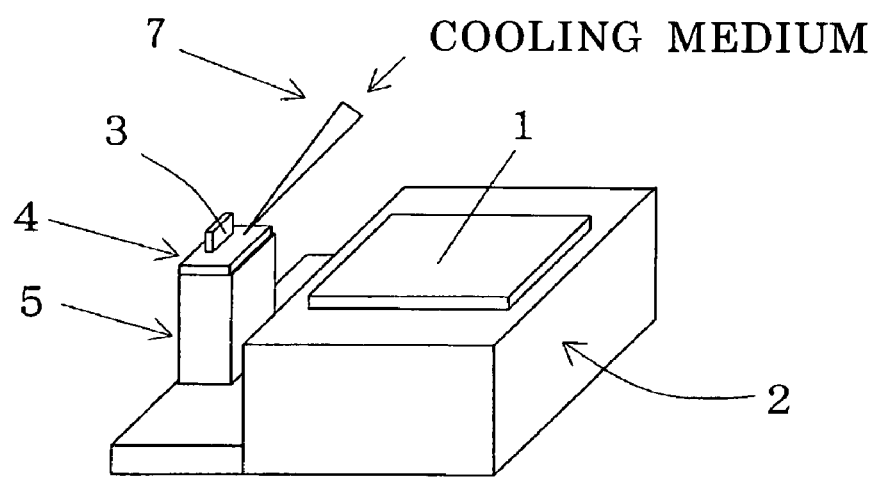
FIG. 2 is a perspective view depicting the micro sample stage and the sample stage of the processing apparatus using the focused charged particle beam according to the first embodiment of the invention.
Figure 3:
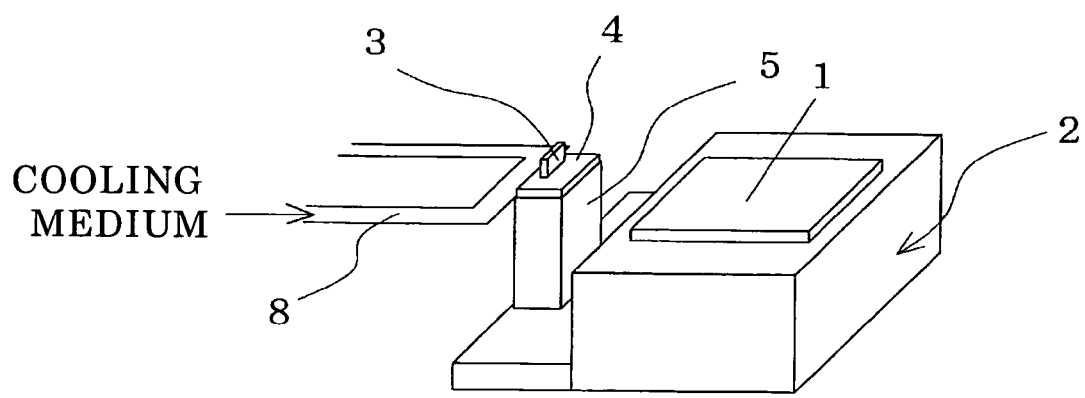
FIG. 3 is a perspective view depicting the micro sample stage and the sample stage of the processing apparatus using the focused charged particle beam according to the first embodiment of the invention.

FIGS. 1 to 3 show the detail of a micro sample stage and a sample stage of a processing apparatus using a focused charged particle beam according to a first embodiment of the invention. The first embodiment is an exemplary implementation provided with the micro sample stage and the sample stage.

FIG. 1 shows the case in which an electronic cooling mechanism is used for a cooling unit. FIG. 2 shows the case in which a probe filled with a cooling medium is used for a cooling unit. FIG. 3 shows the case in which a cooling tube containing a cooling medium is used for a cooling unit.

As shown in FIGS. 1 to 3, the processing apparatus using the focused charged particle beam according to the embodiment is provided with a sample 1 which is processed with a focused charged particle beam, and a sample stage 2 on which the sample 1 is placed. A micro sample 3 which is cut out of the sample 1 with the focused charged particle beam is placed on a micro mount part 4. The micro mount part 4 is provided on a micro sample stage 5. The micro sample stage 5 is supported by the sample stage 2 or provided beside the sample stage 2. The combination of the micro mount part 4 and the sample stage 5 is smaller than the sample stage 1. The micro mount part 4 is formed of a material having a lower heat conduction than that of the micro sample stage 5, and is thermally independent of the micro sample stage 5. Thus, the micro mount part 4 is cooled separately from the micro sample stage 5, and the cooling effect can be prevented from running off to the micro sample stage 5 which is adjacent to the micro mount part 4. Therefore, the sample mount part 4 is cooled by a cooling unit (any one of an electronic cooling mechanism 6, a fine tube or a probe 7, and a cooling tube 8), and thus only the micro mount part 4 is cooled with no reduction in the cooling effect due to heat conduction to the other members. The micro sample 3 is a micro piece which is cut out of the sample 1. Therefore, the sample itself is minute, and has small expansion and contraction caused by heating and cooling. Therefore, a reduction in processing accuracy caused by a thermal drift can be prevented. In addition, the micro mount part 4 on which the micro sample 3 being a micro piece is placed is significantly small as well. Therefore, only the micro mount part 4 can be cooled which is very small and thermally independent of the micro sample stage 5, and thus the micro sample 3 is cooled promptly.

The micro sample stage 5 according to the embodiment is supported by the sample stage 2, but they may be independent separately. In addition, in the embodiment, the micro sample 3 is considered to be cut out of the sample 1, but it may not be cut out as long as it can be placed on the micro mount stage 4. Alternatively, the sample 1 is not necessarily placed on the sample stage 2.

For the example of the sample cooling unit, as shown in FIGS. 1 to 3, the following is named: the electronic cooling mechanism 6, the fine tube or the probe 7 which is abutted against the micro mount stage 4, and the cooling tube 8 which is disposed on the micro mount stage 4 and through which the cooling medium flows. For an example of the electronic cooling mechanism, a Peltier element and the like are named, and for the cooling medium filled in the probe 7 or the cooling tube 8, liquid nitrogen and the like are named. The cooling unit, the electron cooling mechanism, and the coolant are not limited to the units and the materials described above, and other units and materials may be used.

Second Embodiment

Figure 4:
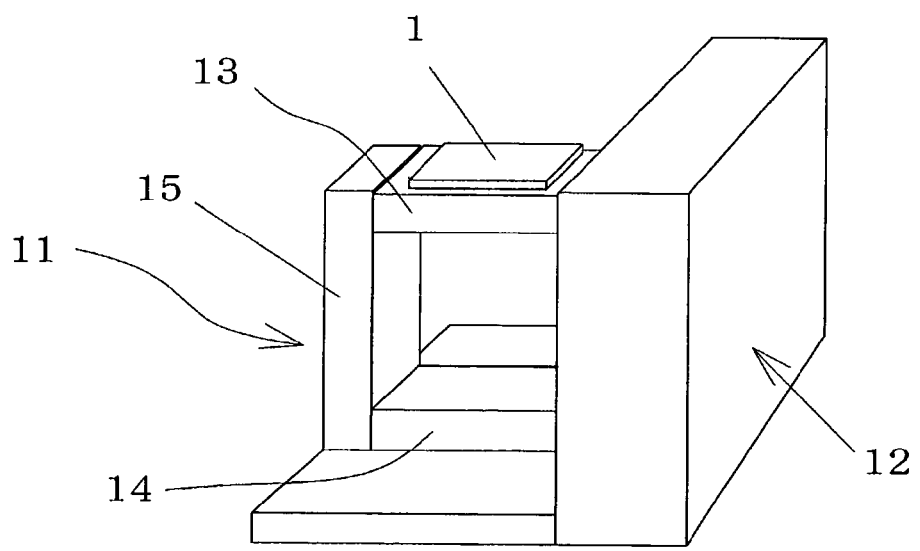
FIG. 4 is a perspective view depicting the special mount stage and the special mount stage support of the processing apparatus using the focused charged particle beam according to the second embodiment of the invention.
Figure 5:
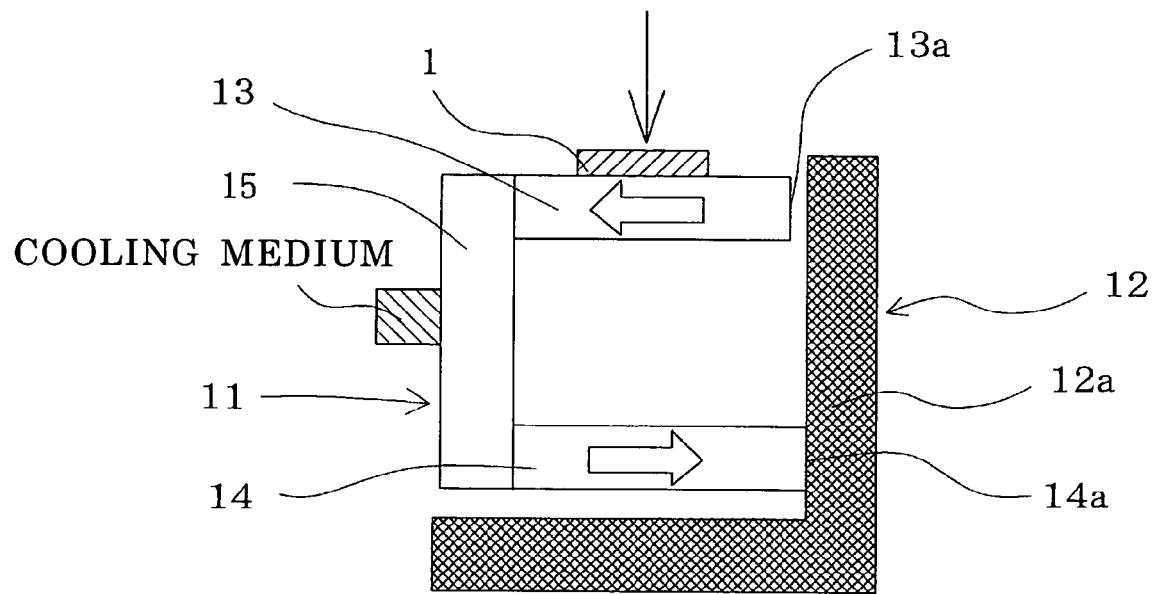
FIG. 5 is a diagram illustrative of the special mount stage and the special mount stage support of the processing apparatus using the focused charged particle beam according to the second embodiment of the invention.

FIGS. 4 to 5 show the detail of a special mount stage and a special mount stage support of a processing apparatus using a focused charged particle beam according to a second embodiment of the invention. The second embodiment is an exemplary implementation provided with the special mount stage and the special mount stage support.

FIG. 4 shows a perspective view depicting the special mount stage and the special mount stage support, and FIG. 5 shows a diagram illustrative of the special mount stage and the special mount stage support.

As shown in FIGS. 4 to 5, the processing apparatus using the focused charged particle beam according to the embodiment is provided with a special mount stage 11 on which a sample 1 processed with a focused charged particle beam is placed, and a special mount stage support 12 in an L-shape which supports the special mount stage 11. The special mount stage 11 is configured of a top plate 13 on which the sample is directly placed, a bottom plate 14 which is in parallel with the top plate 13, and a connecting member 15 which connects one end of the top plate 13 and the bottom plate 14 to each other. An end part 14a of the bottom plate 14 on the opposite side of the connecting member 15 is fixed to a vertical wall part 12a in an L-shape. In addition, an end part 13a of the top plate 13 on the opposite side of the connecting member 15 is not fixed to the vertical wall part 12a in an L-shape, which is in a free state. The special mount stage support 12 is formed of a material having a lower heat conductivity than that of the special mount stage 11, and the special mount stage 11 is thermally independent of the special mount stage support 12. The connecting member 15 is abutted against a cooling unit. Therefore, the special mount stage 11 is cooled by the cooling unit, and thus only the special mount stage 11 is cooled with no reduction in the cooling effect caused by heat conduction to the other members. For the cooling unit, the same means as similar to that of the first embodiment, and the connecting member 15 is cooled by the cooling mechanism. Since one of the end parts of the top plate 13 or the bottom plate 14 of the special mount stage 11 is fixed to the special mount stage support 12 (in the exemplary implementation, the end part on the bottom plate side), the connecting member is cooled to direct the thermal contraction directions of the top plate 13 and the bottom plate 14 opposite to each other as shown in arrows in the drawing. More specifically, since the end part on the bottom plate 14 side is fixed to the special mount stage support 12, the bottom plate 14 shrinks in the right direction in the drawing, and the top plate 13 shrinks in the left direction in the drawing. Therefore, even though the sample is not minute as in the first embodiment, a drift caused by thermal contraction can be relaxed, and a reduction in processing accuracy can be prevented.

Third Embodiment

Figure 6:
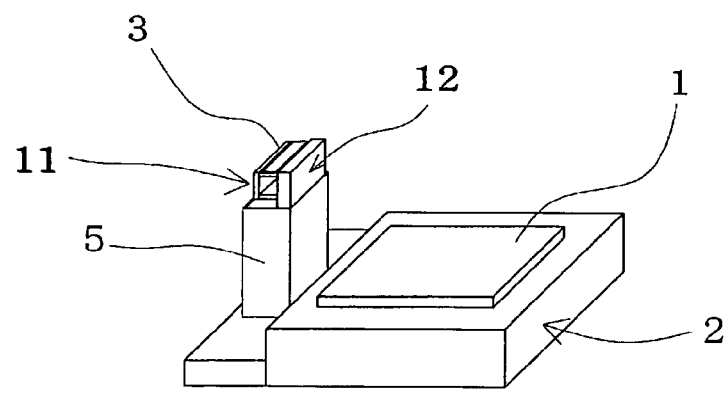
FIG. 6 is a perspective view depicting the case in which the special mount stage and the special mount stage support of the processing apparatus using the focused charged particle beam according to the second embodiment is placed on the micro sample stage according to the first embodiment of the invention.

FIG. 6 relates to a third embodiment according to the invention, which shows a perspective view depicting a micro sample stage and a sample stage in which the special mount stage and the special mount stage support according to the second embodiment are disposed on the micro sample stage according to the first embodiment of the invention. The third embodiment is an exemplary implementation provided with the special mount stage and the special mount stage support on the sample stage.

As shown in FIG. 6, the embodiment shows an example that the special mount stage support 12 shown in FIGS. 4 to 5 is supported by the micro sample stage 5 according to the first embodiment. A sample 1 is placed on a sample stage 2, a micro sample stage 5 is supported by the sample stage 2, and a special mount stage support 12, a special mount stage 11 and a micro sample 3 are supported by the micro sample stage 5. Since the sample itself is minute, a drift caused by thermal contraction is small, and a drift is further relaxed by the structure of the special mount stage 11 and the special mount stage support 12. The effect of preventing a reduction in processing accuracy can be more improved. The special mount stage support 12 and the special mount stage 11 supported by the micro sample stage 5 are also minute, and the connecting member 15 configuring the special mount stage 11 (see FIGS. 4 and 5) can be cooled promptly.

Also in the embodiment, the micro sample stage 5 is supported by the sample stage 2, but they may be independent separately. In addition, in the embodiment, the micro sample 3 may not be cut out of the sample 1, and the sample 1 is not necessarily placed on the sample stage 2.

Fourth Embodiment

Figure 7:
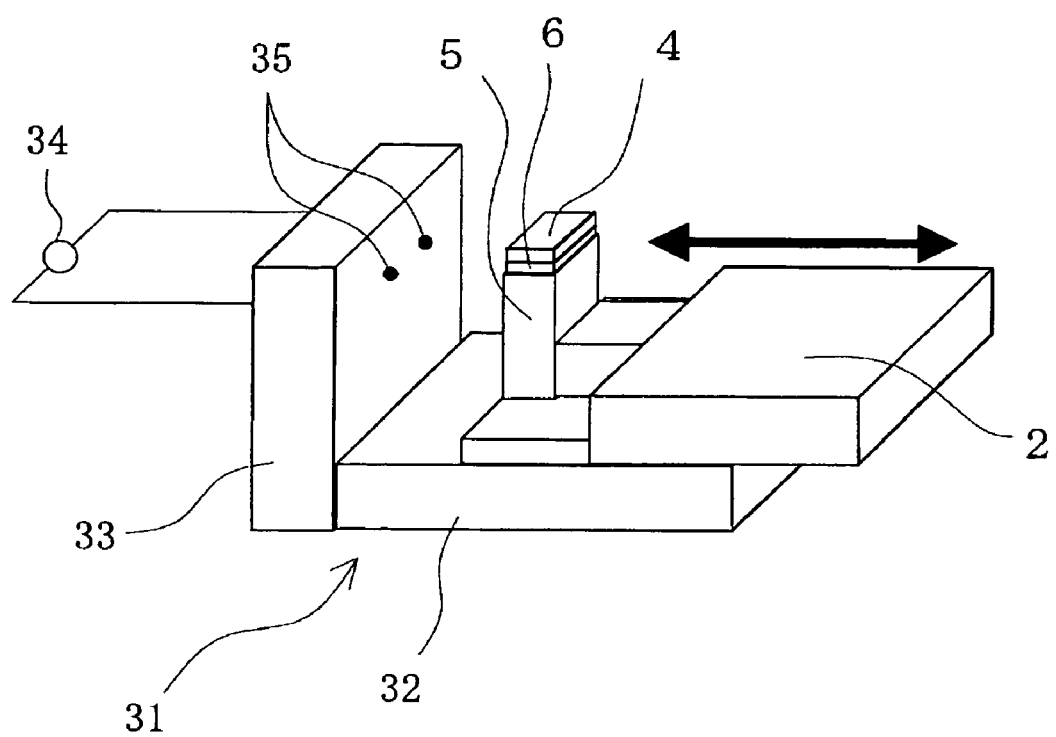
FIG. 7 is a perspective view depicting the movable sample stage of the processing apparatus using the focused charged particle beam according to the third embodiment of the invention.

FIG. 7 shows a perspective view depicting a movable sample stage of a processing apparatus using a focused charged particle beam according to a fourth embodiment of the invention. The fourth embodiment is an example that the sample stage 2 according to the first embodiment is placed on a movable sample stage 31, and the sample stage 2 is provided with the micro sample stage 5 having the electronic cooling mechanism 6 shown in FIG. 1.

As shown in the drawing, the movable sample stage 31 is provided with a base plate 32 which is a component on the apparatus main body side and which holds a sample stage 2 and a micro sample stage 5 formed in one piece with the sample stage 2 (hereinafter, called a sample stage 2) and moves them in reciprocating motion in the directions (indicated by arrows in the drawing). The sample stage 2 is formed detachably on one end side with respect to the base plate 32 (on the right side in the drawing).

Thus, the sample stage 2 can be replaced separately with respect to the apparatus main body side.

A contact 33 is integrally disposed on the other end side of the base plate 32 (on the left side in the drawing), and a power source connecting part 35 is disposed on the contact 33. To the power source connecting part 35, electric power is supplied from a power source 34.

The sample stage 2 is slidably held on the base plate 32. Thus, a power source connecting part (not shown) of the electronic cooling mechanism 6 is connected to the power source connecting part 35 at a predetermined slide position, and electric power from the power source 34 is supplied to the electronic cooling mechanism 6. Therefore, it is unnecessary that the sample stage 2 itself is provided with an electric power supply source. Thus, the configuration of the sample stage 2 can be simplified as well as the sample stage 2 can be replaced easily.

In addition, in FIG. 7, the movable sample stage 31 is taken and described as an example which holds the sample stage 2 shown in FIG. 1, but the sample stage 2 shown in FIG. 3, that is, the sample stage 2 integrally formed with the micro sample stage 5 having the cooling tube 8 may be adapted as well. In this case, to the contact 33, instead of the power source connecting part 35, a liquid nitrogen supply port is provided which is connected to the cooling tube 8, and a passage from an external supply source is connected to the liquid nitrogen supply port.

In addition, a device having the special sample stage 11 shown in FIGS. 4 and 5 may be detachable with respect to the base plate 32. In this case, when the electronic cooling mechanism is adapted as the cooling unit, the contact 33 having the power source connecting part 35 shown in FIG. 7 is used. When the cooling tube through which liquid nitrogen flows is adapted, the contact having the liquid nitrogen supply port is used. Furthermore, the sample stage 2 shown in FIG. 6 may be detachable with respect to the base plate 32, which can be also used for the sample stage with no cooling mechanism.

The invention can be used in the industrial fields of the processing apparatus using the focused charged particle beam having the cooling mechanism which can promptly cool a sample can relax a thermal drift.

What is claimed is:

1. A processing apparatus using a focused charged particle beam, comprising:
a micro sample stage having a micro mount part on which a micro sample is placed for processing with the focused charged particle beam,
wherein the micro mount part is thermally independent of the micro sample stage and has a cooling unit which cools the micro mount part.

2. The processing apparatus using the focused charged particle beam according to claim 1, further comprising a sample stage on which a sample is placed for processing with the focused charged particle beam.

3. The processing apparatus using the focused charged particle beam according to claim 2, wherein the micro sample is cut out of the sample.

4. The processing apparatus using the focused charged particle beam according to claim 2, further comprising a sample stage holder on which the sample stage or the micro sample stage is detachably placed.

5. The processing apparatus using the focused charged particle beam according to claim 2, further comprising a sample stage holder on which the sample stage and the micro sample stage having the cooling unit are detachably placed, wherein the sample stage holder is provided with a contact which is connected to the cooling unit to supply a cooling source.

6. The processing apparatus using the focused charged particle beam according to claim 1, wherein the micro sample stage which is formed of a material having a lower heat conduction than that of the micro mount part.

7. The processing apparatus using the focused charged particle beam according to claim 6, wherein the cooling unit is an electronic cooling mechanism which cools by supplying electric power thereto.

8. The processing apparatus using the focused charged particle beam according to claim 6, wherein the cooling unit is a probe in which a cooling medium is filled and which is abutted against the micro mount part.

9. The processing apparatus using the focused charged particle beam according to claim 6, wherein the cooling unit is a cooling tube which is disposed on the micro mount part and through which a cooling medium flows.

10. A processing apparatus using a focused charged particle beam, comprising:
a top plate on which a sample is placed for processing with the focused charged particle beam; and
a bottom plate which is disposed in parallel with the top plate,
wherein a special mount stage is formed by connecting the top plate to the bottom plate with a connecting member,
the special mount stage is supported by a special mount stage support which is formed of a material having a lower heat conduction than the special mount stage,
one of the top plate and the bottom plate is fixed on a side of the special mount stage support, and
whereby a cooling unit is provided which cools the connecting member and which directs thermal contraction directions of the top plate and the bottom plate in directions opposite to each other.

11. The processing apparatus using the focused charged particle beam according to claim 10, further comprising a sample stage on which the sample is placed for processing with the focused charged particle beam.

12. The processing apparatus using the focused charged particle beam according to claim 11 further comprising a sample stage holder on which the sample stage or the special mount stage support is detachably placed.

13. The processing apparatus using the focused charged particle beam according to claim 12, wherein the sample stage holder is provided with a contact which is connected to the cooling unit to supply a cooling source.

14. The processing apparatus using the focused charged particle beam according to claim 10, wherein the cooling unit is an electronic cooling mechanism which cools by supplying electric power thereto.

15. The processing apparatus using the focused charged particle beam according to claim 10, wherein the cooling unit is a probe in which a cooling medium is filled and which is abutted against the connecting member.

16. The processing apparatus using the focused charged particle beam according to claim 10, wherein the cooling unit is a cooling tube which is disposed on the connecting member and through which a cooling medium flows.

17. A processing apparatus using a focused charged particle beam, comprising:

a first sample stage;

a second sample stage smaller than the first stage and provided beside the first sample stage; and cooling means for cooling the second sample stage.

18. A processing apparatus using the focused charged particle beam according to claim 17, wherein the second sample stage has at least two layers, an upper layer of the at least two layers has higher thermal conductivity than a lower layer of the at least two layers, and the upper layer of the at least two layers is cooled by the cooling means.

* * * * *